US012661493B2

(12) United States Patent
Hoover et al.

(10) Patent No.: US 12,661,493 B2
(45) Date of Patent: Jun. 23, 2026

(54) ASEPTIC CONNECTOR WITH DISPOSABLE AIR LOCK

(71) Applicant: CENTRE FOR COMMERCIALIZATION OF REGENERATIVE MEDICINE, Toronto (CA)

(72) Inventors: Spencer Hoover, Winchester, MA (US); Calley Hirsch, Toronto (CA); Rajan Ramanuj, Mississauga (CA)

(73) Assignee: CENTRE FOR COMMERCIALIZATION OF REGENERATIVE MEDICINE, Toronto (CA)

( * ) Notice: Subject to any disclaimer, the term of this patent is extended or adjusted under 35 U.S.C. 154(b) by 411 days.

(21) Appl. No.: 18/281,917

(22) PCT Filed: Mar. 15, 2022

(86) PCT No.: PCT/CA2022/050382
§ 371 (c)(1),
(2) Date: Sep. 13, 2023

(87) PCT Pub. No.: WO2022/193000
PCT Pub. Date: Sep. 22, 2022

(65) Prior Publication Data
US 2024/0149041 A1 May 9, 2024

Related U.S. Application Data

(60) Provisional application No. 63/161,200, filed on Mar. 15, 2021.

(51) Int. Cl.
*A61M 39/18* (2006.01)
*A61M 39/10* (2006.01)

(52) U.S. Cl.
CPC ..... *A61M 39/18* (2013.01); *A61M 2039/1072* (2013.01); *A61M 2039/1077* (2013.01)

(58) Field of Classification Search
CPC .......... A61M 39/18; A61M 2039/1072; A61M 2039/1077
See application file for complete search history.

(56) References Cited

U.S. PATENT DOCUMENTS

| | | | | |
|---|---|---|---|---|
| 4,354,490 A | 10/1982 | Rogers | | |
| 5,395,351 A | * 3/1995 | Munsch | ................. | F16L 37/33 |
| | | | | 604/167.03 |
| 5,820,614 A | * 10/1998 | Erskine | .............. | F16L 55/1007 |
| | | | | 604/905 |
| 8,992,489 B2 | * 3/2015 | Spohn | ................... | A61M 5/007 |
| | | | | 137/460 |
| 10,022,532 B2 | * 7/2018 | Burdge | .................. | F16L 37/35 |

(Continued)

FOREIGN PATENT DOCUMENTS

GB         2343723 A      5/2000

*Primary Examiner* — Dung T Ulsh
(74) *Attorney, Agent, or Firm* — Smart & Biggar LP; Carmela De Luca

(57) ABSTRACT

Described herein are systems for an aseptic connector, including a reusable aseptic connector. A connector system is provided for establishing the aseptic fluid connection. The connector system includes a first connector, a second connector and an airlock. Also provided is an air lock and a connector, as well as methods of use thereof.

13 Claims, 2 Drawing Sheets

(56) References Cited

U.S. PATENT DOCUMENTS

| | | | |
|---|---|---|---|
| 2010/0049160 A1* | 2/2010 | Jepson | A61M 5/162 |
| | | | 604/415 |
| 2011/0240158 A1* | 10/2011 | Py | F16L 41/02 |
| | | | 29/428 |
| 2012/0116294 A1 | 5/2012 | Boenig et al. | |
| 2020/0237621 A1 | 7/2020 | Naygauz et al. | |

* cited by examiner

Figure 3:
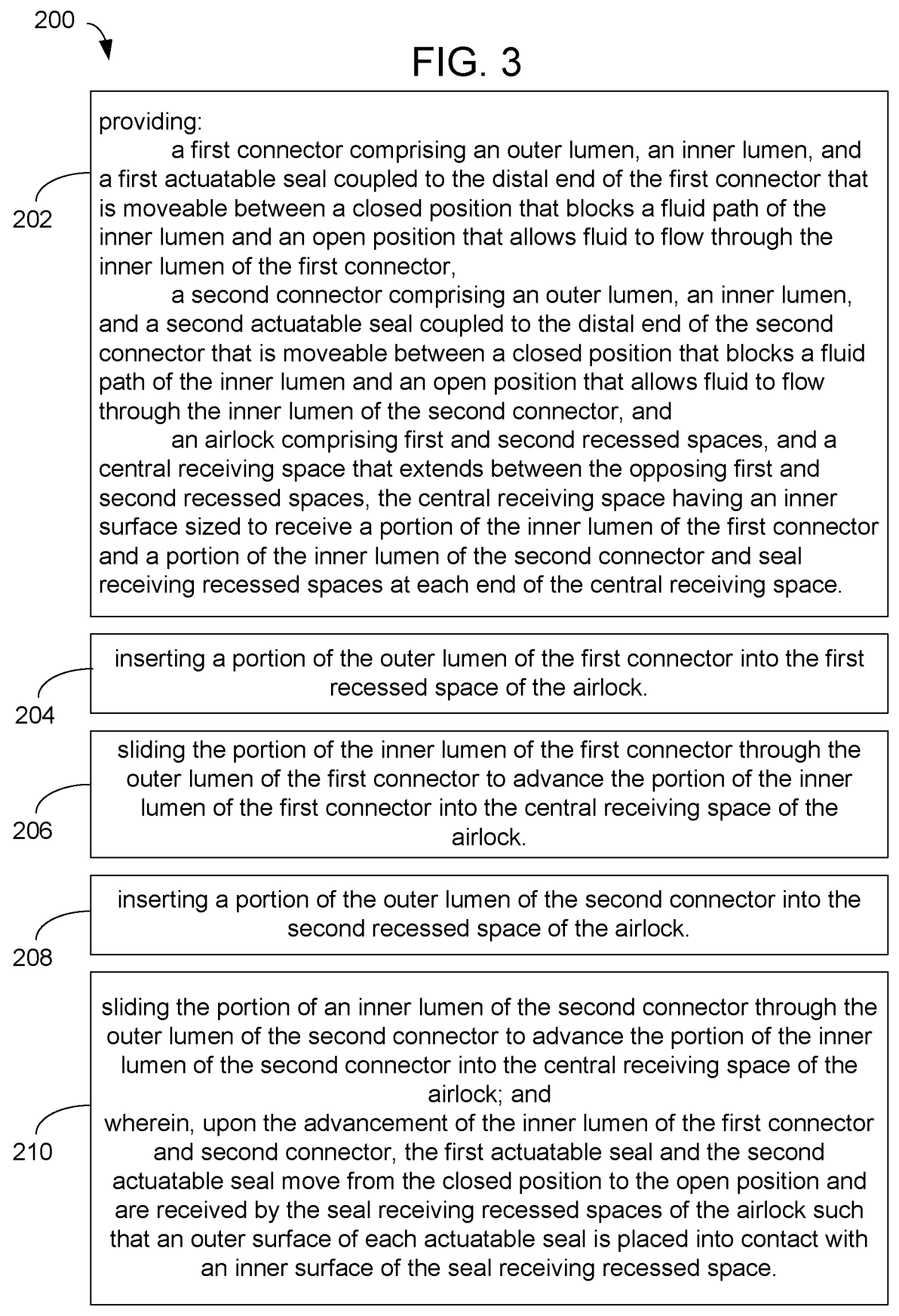

202 providing:
    a first connector comprising an outer lumen, an inner lumen, and a first actuatable seal coupled to the distal end of the first connector that is moveable between a closed position that blocks a fluid path of the inner lumen and an open position that allows fluid to flow through the inner lumen of the first connector,
    a second connector comprising an outer lumen, an inner lumen, and a second actuatable seal coupled to the distal end of the second connector that is moveable between a closed position that blocks a fluid path of the inner lumen and an open position that allows fluid to flow through the inner lumen of the second connector, and
    an airlock comprising first and second recessed spaces, and a central receiving space that extends between the opposing first and second recessed spaces, the central receiving space having an inner surface sized to receive a portion of the inner lumen of the first connector and a portion of the inner lumen of the second connector and seal receiving recessed spaces at each end of the central receiving space.

204 inserting a portion of the outer lumen of the first connector into the first recessed space of the airlock.

206 sliding the portion of the inner lumen of the first connector through the outer lumen of the first connector to advance the portion of the inner lumen of the first connector into the central receiving space of the airlock.

208 inserting a portion of the outer lumen of the second connector into the second recessed space of the airlock.

210 sliding the portion of an inner lumen of the second connector through the outer lumen of the second connector to advance the portion of the inner lumen of the second connector into the central receiving space of the airlock; and
wherein, upon the advancement of the inner lumen of the first connector and second connector, the first actuatable seal and the second actuatable seal move from the closed position to the open position and are received by the seal receiving recessed spaces of the airlock such that an outer surface of each actuatable seal is placed into contact with an inner surface of the seal receiving recessed space.

ASEPTIC CONNECTOR WITH DISPOSABLE AIR LOCK

RELATED APPLICATIONS

This application is a national phase entry of PCT/CA2022/050382, filed Mar. 15, 2022, which claims priority from U.S. Provisional patent application Ser. No. 63/161,200 filed Mar. 15, 2021, each of these applications being incorporated herein in their entirety by reference.

BACKGROUND

Aseptic connectors can be used to connect two or more sterilized fluid pathways. For example, aseptic connectors can be used to couple a fluid pathway from a first piece of processing equipment to a second piece of processing equipment to establish a sterile pathway for fluid transfer between each piece of process equipment. Aseptic connectors are used in various industries, such as biopharmaceutical, bioprocessing, and medical applications. In these industries, maintaining an aseptic environment can be of critical importance when transferring fluids to prevent contamination of the transport fluid to disease-causing microorganisms (e.g., fungi, bacteria, viruses, spores).

Many single use aseptic connectors exist on the market for small tubing, and multiuse connectors exist for large tubing. The single use connectors are costly and can have limited utility since they may only be aseptically connected once prior to disposal. Attempts have been made to produce a multi-use aseptic connector. However, such attempts have created connectors that often fail after only a few connection cycles and can leak residual fluid upon disconnection. Of further concern, these previous connectors often suffer from additional complications, such as having bulky or complex configurations that take a long time to connect, are limited to large tubing (e.g., not compatible with specific applications, such as autologous therapies), are not automation friendly, and typically include gendered connections. Other connectors exist that are genderless, but are only used for a single connection, or only one side of the connector is able to carry out multiple connections.

Additionally, tube welding exists as a mechanism to produce aseptic connections. Drawbacks of tube welding include not being able to weld multiple sizes and types of tubing together, and the occasional generation of particulates into the fluid system.

SUMMARY OF THE DISCLOSURE

The present disclosure addresses the aforementioned drawbacks by providing systems and methods for aseptic fluid connection using a connector system. The connector system described herein can provide multiple sterile connections and reconnections. The connector system may provide genderless connections, which facilitates reducing user error during connections and promotes ease of assembly. The provided connector system is compatible with automation, and is adaptable to multiple sizes of tubing, both large and small (e.g., suitable for use with autologous therapies). Further, the provided connector system may include disposable components making the provided connector system cost effective. The provided connector system may be used without external films or covers, allowing multiple sterile connections to occur.

In one aspect, the present disclosure provides a connector system. The connector system includes a first connector extending between a distal end and a proximal end. The first connector includes an outer lumen, an inner lumen that is slideable within the outer lumen of the first connect, and a first actuatable seal coupled to the distal end of the first connector. The first actuatable seal coupled to the distal end of the first connector is moveable between a closed position that blocks a fluid path of the inner lumen and an open position that allows fluid to flow through the inner lumen of the first connector. The connector system further includes a second connector extending between a distal end and a proximal end. The second connector includes an outer lumen, an inner lumen that is slideable within the outer lumen of the second connector, and a second actuatable seal coupled to the distal end of the second connector. The second actuatable seal is moveable between a closed position that blocks a fluid path of the inner lumen and an open position that allows fluid to flow through the inner lumen of the second connector.

The connector system further includes an airlock comprising a body having opposing first and second recessed spaces. The first recessed space is sized to slidably receive a portion of the outer lumen of the first connector, and the second recessed space is sized to slidably receive a portion of the outer lumen of the second connector. The airlock includes a central receiving space that extends between the opposing first and second recessed spaces. The central receiving space includes an inner surface sized to receive a portion of the inner lumen of the first connector and a portion of the inner lumen of the second connector. The central receiving space further includes seal receiving recessed spaces at each end of the central receiving space that are sized to receive the first and second actuatable seals. The inner lumen of the first connector and the inner lumen of the second connector are slidable to advance into the central receiving space of the airlock. Upon advancement of the inner lumen of the first connector and the second connector, the first actuatable seal and the second actuatable seal move from the closed position to the open position and are received by the seal receiving recessed spaces of the airlock such that an outer surface of each actuatable seal is placed in contact with an inner surface of the seal receiving recessed space.

In one or more embodiments, the airlock may further comprise opposing mechanical seals spanning each recessed space in the body to enclose the central receiving space, the mechanical seals may be moveable upon application of external force thereupon in order to form an opening to allow the inner lumen of the first connector and the inner lumen of the second connector to enter the central receiving space and be placed in fluid communication.

In one or more embodiments, each mechanical seal may comprise a first and second leaflet that are biased in a closed position to prevent fluid flow within the central receiving space.

In one or more embodiments, each mechanical seal may comprise a destroyable membrane.

In one or more embodiments, each actuatable seal may be biased with a spring such that operation of the spring moves the actuatable seal between the closed position and the open position.

In one or more embodiments, each actuatable seal may comprise a first leaflet and a second leaflet, wherein the first and second leaflets may be movable between the closed position and the open position.

In one or more embodiments, when in the open position each actuatable seal may extend outward from the distal end of the outer lumen of the connector.

In one or more embodiments, each actuatable seal may be moveable from the closed position to the open position when an external force is applied to an internal surface of the actuatable seal.

In one or more embodiments, the proximal end of the first connector and the second connector may be adapted to receive tubing.

In one or more embodiments, the central receiving space of the airlock may be sterile.

In one or more embodiments, the central receiving space may include a gasket configured to receive the inner lumen of the first connector and the inner lumen of the second connector.

In one or more embodiments, the gasket may seal a distal end of the inner lumen of the first connector to a distal end of the inner lumen of the second connector.

In one or more embodiments, when the outer surface of each actuatable seal is placed into contact with the inner surface of the seal receiving recessed space aseptic fluid connection may be provided.

In another aspect, the present disclosure provides an airlock. The airlock includes a body comprising opposing recessed spaces each having an opening at an outer surface of the body. The opposing recessed space include side walls that extend from the opening at the outer surface of the body to a base surface within the body. The airlock includes a central receiving space having an inner surface that extends through the body to connect the opposing recessed spaces. The airlock including opposing mechanical seals spanning each opening in the body to enclose the central receiving space, the mechanical seals being moveable upon application of external force thereupon in order to form an opening to allow the inner lumen of the first connector and the inner lumen of the second connector to enter the central receiving space and be placed in fluid communication.

In one or more embodiments, each mechanical seal may comprise first and second leaflets that may be biased to be in a closed position to prevent fluid flow within the central receiving space.

In one or more embodiments, each mechanical seal may comprise a destroyable membrane.

In one or more embodiments, the inner surface of the central receiving space may have recessed spaces formed therein at each end of the central receiving space and extending away from a central axis of the central receiving space.

In one or more embodiments, the central receiving space may be sterile.

In some aspects, the present disclosure provides an airlock for providing an aseptic fluid connection, comprising: a body comprising opposing recessed spaces each having an opening at an outer surface of the body, each opposing recessed space having side walls that extend from the opening at the outer surface of the body to a base surface within the body; a central receiving space having an inner surface that extends through the body to connect the opposing recessed spaces; and opposing mechanical seals spanning each opening in the body to enclose the central receiving space, the mechanical seals being moveable upon application of external force thereupon in order to form an opening to provide access to the central receiving space.

In one or more embodiments, each mechanical seal may comprise first and second leaflets that may be biased to be in a closed position to prevent fluid flow within the central receiving space.

In one or more embodiments, each mechanical seal may comprise a destroyable membrane.

In one or more embodiments, the inner surface of the central receiving space may have recessed spaces formed therein at each end of the central receiving space and extending away from a central axis of the central receiving space.

In one or more embodiments, the central receiving space may be sterile.

In one or more embodiment, the airlock may be for providing aseptic fluid connection In some aspects, the present disclosure provides a connector. The connector includes an outer lumen extending between a distal end and a proximal end. The outer lumen includes a stop surface at the distal end that protrudes from an inner surface of the outer lumen towards a central axis of the outer lumen. The connector includes an inner lumen extending between a distal end and a proximal end. The inner lumen includes a stop surface defined by a recessed region positioned along the distal end. The inner lumen is slidable within the outer lumen along a distance between the stop surface of the inner lumen and the stop surface of the outer lumen. The connector further includes an actuatable seal coupled to the distal end of the outer lumen. The actuatable seal is movable from a closed position that blocks a fluid path of the inner lumen and an open position that allows fluid to flow through the inner lumen.

In one or more embodiments, the actuatable seal may be biased with a spring such that operation of the spring may move the actuatable seal between the closed position and the open position.

In one or more embodiments, the actuatable seal may comprise a first leaflet and a second leaflet, wherein the first and second leaflets may be slidably movable between closed position and the open position.

In one or more embodiments, when in the open position the actuatable seal may extend outward from the distal end of the outer lumen.

In one or more embodiments, the actuatable seal may be moveable from the closed position to the open position when an external force is applied to an internal surface of the actuatable seal.

In one or more embodiments, the proximal end of the connector may be adapted to receive tubing.

In one or more embodiments, the connector may be for providing aseptic fluid connection.

In some aspects, there is provided a method for using a connector system, comprising: providing: a first connector comprising an outer lumen, an inner lumen, and a first actuatable seal coupled to the distal end of the first connector that is moveable between a closed position that blocks a fluid path of the inner lumen and an open position that allows fluid to flow through the inner lumen of the first connector, a second connector comprising an outer lumen, an inner lumen, and a second actuatable seal coupled to the distal end of the second connector that is moveable between a closed position that blocks a fluid path of the inner lumen and an open position that allows fluid to flow through the inner lumen of the second connector, and an airlock comprising first and second recessed spaces, and a central receiving space that extends between the opposing first and second recessed spaces, the central receiving space having an inner surface sized to receive a portion of the inner lumen of the first connector and a portion of the inner lumen of the second connector and seal receiving recessed spaces at each end of the central receiving space; inserting a portion of the outer lumen of the first connector into the first recessed space of the airlock; sliding the portion of the inner lumen of the first connector through the outer lumen of the first connector to advance the portion of the inner lumen of the first connector into the central receiving space of the airlock; inserting a portion of the outer lumen of the second connector into the second recessed space of the airlock; sliding the portion of an inner lumen of the second connector through the outer lumen of the second connector to advance the portion of the inner lumen of the second connector into the central receiving space of the airlock; and wherein, upon the advancement of the inner lumen of the first connector and second connector, the first actuatable seal and the second actuatable seal move from the closed position to the open position and are received by the seal receiving recessed spaces of the airlock such that an outer surface of each actuatable seal is placed into contact with an inner surface of the seal receiving recessed space.

In one or more embodiments, the airlock may further comprises opposing mechanical seals spanning each recessed space in the body to enclose the central receiving space, the mechanical seals being moveable upon application of external force thereupon in order to form an opening which may allow the inner lumen of the first connector and the inner lumen of the second connector to enter the central receiving space and be placed in fluid communication.

In one or more embodiments, each mechanical seal may comprise a first and second leaflet that are biased in a closed position to prevent fluid flow within the central receiving space.

In one or more embodiments, each mechanical seal may comprise a destroyable membrane.

In one or more embodiments, each actuatable seal may be biased with a spring such that operation of the spring moves the actuatable seal between the closed position and the open position.

In one or more embodiments, each actuatable seal may comprise a first leaflet and a second leaflet, wherein the first and second leaflets are movable between the closed position and the open position.

In one or more embodiments, when in the open position each actuatable seal may extend outward from the distal end of the outer lumen of the connector.

In one or more embodiments, each actuatable seal may be moveable from the closed position to the open position when an external force is applied to an internal surface of the actuatable seal.

In one or more embodiments, the proximal end of the first connector and the second connector may be adapted to receive tubing.

In one or more embodiments, the central receiving space of the airlock may be sterile.

In one or more embodiments, the central receiving space may include a gasket configured to receive the inner lumen of the first connector and the inner lumen of the second connector.

In one or more embodiments, the gasket may seal a distal end of the inner lumen of the first connector to a distal end of the inner lumen of the second connector.

In one or more embodiments, when the outer surface of each actuatable seal is placed into contact with the inner surface of the seal receiving recessed space aseptic fluid connection may be provided.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIG. 3 is a method drawing of a method of use of a connector system.

DETAILED DESCRIPTION

Figure 1:
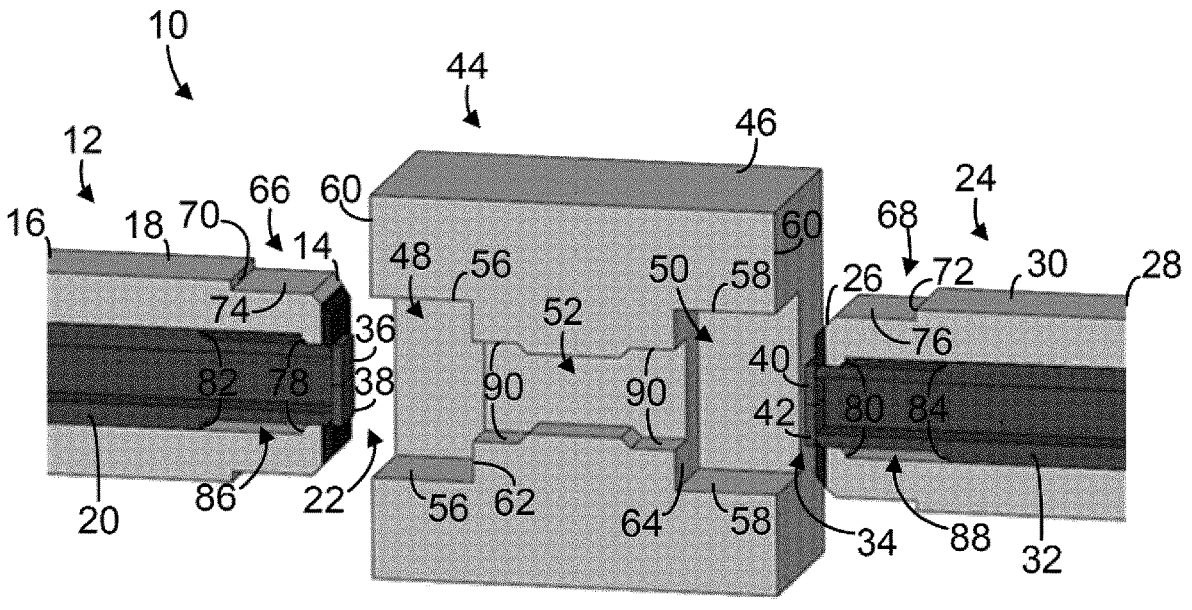
FIG. 1 is a perspective, cross sectional view of an illustration of a connector system in a disconnected, open state.

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, the terms "sterile," "asepsis," and "aseptic" are used interchangeably. The term "aseptic" is defined as the state of being substantially free or entirely free from disease causing microorganisms (e.g., pathogenic bacteria, viruses, pathogenic fungi, and parasites). The term "substantially free" of disease causing microorganisms is defined as having a sterility assurance level (SAL) of $10^{-6}$ or less, which is when a surface, container, or volume has a probability that is less than one out of one million that it is contaminated with replicating microorganisms. The term "aseptic fluid connection" is defined as a connection that prevents a sterile fluid traveling within the aseptic fluid connection from being exposed to external disease causing microorganisms, thereby maintaining an aseptic environment.

As used in this specification and the appended claims, the singular forms "a", "an" and "the" include plural references unless the content clearly dictates otherwise. It should also be noted that the term "or" is generally employed in its sense including "and/or" unless the content clearly dictates otherwise. That is, "X and/or Y" is intended to mean X or Y or both, for example. As a further example, "X, Y, and/or Z" is intended to mean X or Y or Z or any combination thereof.

The definitions and embodiments described in particular sections are intended to be applicable to other embodiments herein described for which they are suitable as would be understood by a person skilled in the art.

Further, the definitions and embodiments described in particular sections are intended to be applicable to other embodiments herein described for which they are suitable as would be understood by a person skilled in the art. For example, in the following passages, different aspects of the disclosure, are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Figure 2:
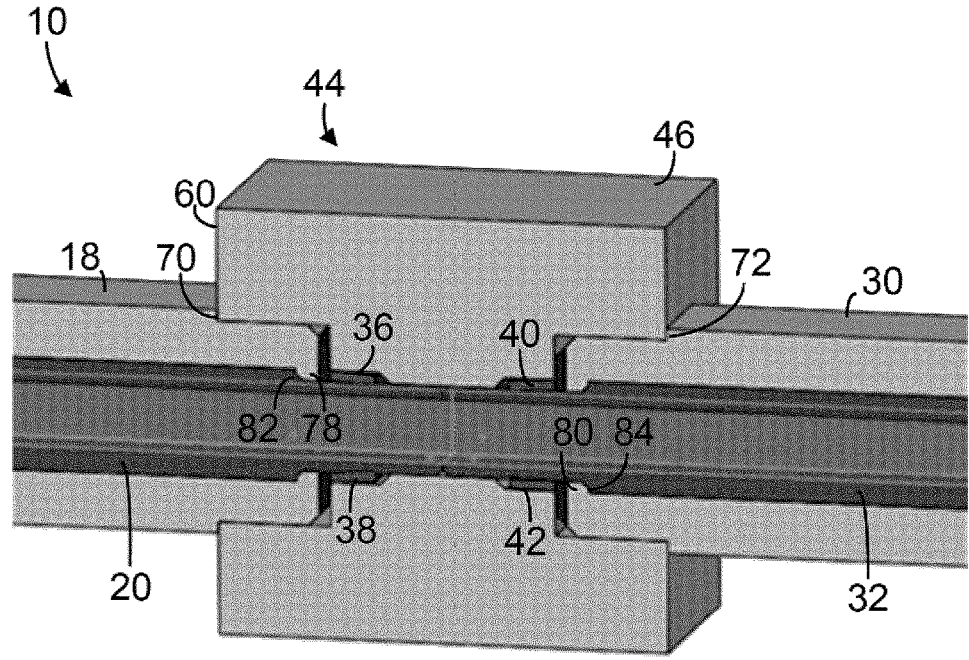
FIG. 2 is a perspective, cross sectional view of an illustration of a connector system in a connected, closed state.

Described here are systems and methods for aseptic fluid connection. Referring to FIGS. 1-2, embodiments of a connector system 10 are depicted in a disconnected, closed state (FIG. 1), and a connected, open state (FIG. 2). The connector system 10 includes a first connector 12 extending between a distal end 14 and a proximal end 16, a second connector 24 extending between a distal end 26 and a proximal end 28, and an airlock 44. In use, the airlock 44 is arranged between the first connector 12 and the second connector 24. When the first and second connectors 12, 24 are engaged with the airlock 44, an aseptic fluid path is provided between the first and second connectors 12, 24. Advantageously, the airlock 44 can be manufactured to be a single-use disposable airlock 44, or as a multi-use airlock 44 (e.g., an airlock 44 that can be sterilized between uses).

The first connector generally 12 includes an outer lumen 18, an inner lumen 20 that is slidable within the outer lumen 18, and a first actuatable seal 22 coupled to the distal end 14 of the first connector 12. The first actuatable seal 22 is moveable between a closed position (e.g., depicted in FIG. 1) in which fluid is blocked from entering or exiting the distal end 14 of the inner lumen 20, and an open position (e.g., depicted in FIG. 2) in which fluid is able to enter and exit the distal end 14 of the inner lumen 20.

The connector system 10 further includes a second connector 24 extending between a distal end 26 and a proximal end 28. The second connector 24 generally includes an outer lumen 30, an inner lumen 32 that is slidable within the outer lumen 30, and a second actuatable seal 34 coupled to the distal end 26 of the second connector 24. The second actuatable seal 34 is moveable between a closed position (e.g., depicted in FIG. 1) in which fluid is blocked from entering or exiting the distal end 26 of the inner lumen 32, and an open position (e.g., depicted in FIG. 2) in which fluid is able to enter and exit the distal end 26 of the inner lumen 32.

The first and second actuatable seals 22, 34 may be selectively opened by applying a force (e.g., and external force) to an internal surface of the respective seal. For instance, the first and second actuatable seals 22, 34 may be selectively opened by advancing, or otherwise moving, the respective inner lumen 20, 32 to directly or indirectly contact the seals 22, 34 to transition the seals 22, 34 from their closed position to their open position. Similarly, in some examples the first and second actuatable seals 22, 34 may be selectively closed by retracting, or otherwise moving, the respective inner lumen 20, 32 to disengage the from the seals 22, 34 in order to transition the seals from their open position to their closed position.

In one non-limiting example, the first actuatable seal 22 includes a first leaflet 36 and a second leaflet 38 that are each coupled to opposing sides of the distal end 14 of the first connector 12, and which each extend from the distal end 14 toward a central axis of the inner lumen 20. When in the closed position, the first leaflet 36 and second leaflet 38 form a fluid-tight seal on engagement. In some embodiments, the first leaflet 36 and the second leaflet 38 are pivotally connected to the distal end 14 of the first connector 12. A biasing member (not depicted in FIGS. 1-2), such as a spring, can be configured to bias the first leaflet 36 and second leaflet 38 in the closed position to prevent fluid from entering or exiting the inner lumen 20. In these instances, upon advancement of the inner lumen 20 (e.g., FIG. 2), the first leaflet 36 and the second leaflet 38 may pivot to transition from the closed position to the open position. In this way, the first leaflet 36 and the second leaflet 38 may act as swinging doors that control fluid flow into and out of the inner lumen 20. The second actuatable seal 34 may include leaflets 40, 42 coupled to the distal end of the second connector 24 and configured in a similar manner as the leaflets 36, 38 of the first actuatable seal 22.

The airlock 44 of the connector system 10 includes a body 46 having a first recessed space 48 and a second recessed space 50 that are both positioned within the body 46. In some embodiments, the first recessed space 48 and the second recessed space 50 are arranged on opposing sides of the body 46. The first recessed space 48 is sized to slidably receive a portion of the outer lumen 18 of the first connector 12, and the second recessed space 50 is sized to slidably receive a portion of the outer lumen 30 of the second connector 24. The airlock 44 includes a central receiving space 52 that extends between the opposing first and second recessed spaces 48, 50. The central receiving space 52 includes an inner surface 54 that is sized to receive a portion of the inner lumen 20 of the first connector 12 and a portion of the inner lumen 32 of the second connector 24.

The first recessed space 48 and second recessed space 50 include first and second side walls 56, 58 that extend from the opening at an outer surface 60 of the body 46 to a respective first and second base surface 62, 64 within the body 46. The first and second base surface 62, 64 serve as a stop surface that engages or abuts against the distal end 14, 26 of the respective outer lumens 18, 30 upon advancement.

In some embodiments, the outer lumens 18, 30 include a respective recessed space 66, 68 positioned on an exterior surface of the distal end 14, 26 that engages or slides against the side walls 56, 58. The outer lumens 18, 30 may each include an exterior stop surface 70, 72 that that protrudes from an exterior surface of the outer lumens 18, 30 to a bottom surface 74, 76 of the recessed space 66, 68. The exterior stop surfaces 70, 72 of the outer lumens 18, 30 engage or abut against the exterior surface 60 of the body 46 upon advancement of the outer lumens 18, 30. The outer lumens 18, 30 may further include an inner stop surface 78, 80 positioned at the distal end 14, 26. The inner stop surface 78, 80 protrudes from an inner surface of the outer lumen 18, 30 towards a central axis of the outer lumen 18, 30.

In some embodiments, the inner lumens 20, 32 include a respective stop surface 82, 84 defined by a recessed region 86, 88 positioned along the distal end. The stop surface 82, 84 may protrude from an exterior surface of the respective inner lumen 20, 32 towards a central axis of the inner lumens 20, 32 to a bottom surface of the recessed space 86, 88. The inner lumens 20, 32 are slideable within the outer lumens 18, 30 along a distance defined by the stop surface 82, 84 of the inner lumen 20, 32 and the interior stop surface 78, 80 of the outer lumen 18, 30.

In some embodiments, the inner surface of the central receiving space 52 includes seal receiving recessed spaces 90 located at each end of the central receiving space 52. The seal receiving recessed spaces 90 are sized to receive the first and second actuatable seals 22, 34. For example, upon advancement of the respective inner lumens 20, 32, the first leaflets 36, 40 and second leaflets 38, 42 of the actuatable seals 22, 34 pivot outward and are received by the seal receiving recessed spaces 90. In some embodiments, the actuatable seals 22, 34 are pressed against the seal receiving recessed spaces 90 with sufficient force to form a fluid-tight seal.

As shown in FIG. 2, when the connector system 10 is in the closed state, the inner lumen 20 of the first connector 12 and the inner lumen 32 of the second connector 24 slidably advance from the respective outer lumens 18, 30 into the central receiving space 52 to engage one another and form a fluid-tight seal. The central receiving space 52 may include gaskets and/or O-rings (not depicted) having openings to receive the inner lumens 20, 32. The gaskets and/or O-rings may enhance the fluid-tight seal in the central receiving space 52 by sealing the connection between distal ends of the inner lumens 20, 32. In some embodiments, the distal ends of the inner lumens 20, 32 are genderless, and may have a flat or substantially flat surface. Genderless connections offer various benefits, such as a reduction in user error on connection and ease of assembly. Although not depicted in FIGS. 1 and 2, in certain embodiments, the distal ends of the inner lumens 20, 32 may be gendered and engage each other with male and female connections.

Although not depicted in FIGS. 1 and 2, the airlock 44 includes mechanical seals spanning each recessed space 48, 50 in the body 46 to enclose the central receiving space 52. The mechanical seals are moveable upon application of external force thereupon (e.g., advancement of the inner lumens 20, 32). Upon application of the external force, the mechanical seals are moveable from a closed position to an open position to allow the inner lumen 20 of the first connector 12 and the inner lumen 32 of the second connector 24 to enter the central receiving space 52, and be placed in fluid communication with one another.

In some embodiments, the mechanical seals comprise first and second leaflets that are biased in the closed position to prevent fluid or external pathogen causing microorganisms from entering the airlock 44. The interior surfaces or volume of the airlock may be sterile, and the mechanical seals may maintain the sterile environment. In some embodiments, the mechanical seals comprise or are composed of destroyable membranes. The mechanical seals may be composed of single use materials, that can be replaced after a single use. Alternatively, the mechanical seals may be used in multiple uses.

The provided connector system 10 offers various advantages over existing systems. First, the provided connector system 10 is capable of multiple sterile connections and reconnections (e.g., at least 1 connection and reconnection, at least 2, at least 3, at least 4, at least 5, or more multiuse connection and reconnections) while maintaining a sterile environment. The connections are genderless, which reduces user connection error and allows facile assembly. The provided connector system 10 is compatible with automation, and may be used with multiple sizes of tubing including small size application, such as autologous therapies. Further, the provided airlock 44 prevents contamination from occurring during the fluid line connection and also prevents any subsequent contamination from occurring in the fluid path during disconnection. The system does not use films or other covers to maintain sterility allowing for multiple connections to occur. Additionally, the airlock 44 may comprise or be composed of disposable or single use components, thereby reducing cost of the system 10.

The systems and methods described in the present disclosure are applicable to any process that benefits from maintaining an aseptic fluid connection. Such processes can include fluid transfer within the medical field, such as the transport of solutions containing cells. As another example, the processes can include fluid transfer within the cell and tissue culturing fields, virus and protein producing fields, and any other related fields where cell-containing fluids, growth media, factors, and so on, may need to be transferred between containers.

Referring next to FIG. 3, there is shown a method diagram 200 for a method of use of the connector system of FIGS. 1 and 2.

A user of the connector system may use the connector system disclosed herein to various fluids, including within the medical field as described above.

At 202, a first connector, second connector and airlock are provided. The first connector comprising an outer lumen, an inner lumen, and a first actuatable seal coupled to the distal end of the first connector that is moveable between a closed position that blocks a fluid path of the inner lumen and an open position that allows fluid to flow through the inner lumen of the first connector. The second connector comprising an outer lumen, an inner lumen, and a second actuatable seal coupled to the distal end of the second connector that is moveable between a closed position that blocks a fluid path of the inner lumen and an open position that allows fluid to flow through the inner lumen of the second connector. The airlock comprising first and second recessed spaces, and a central receiving space that extends between the opposing first and second recessed spaces, the central receiving space having an inner surface sized to receive a portion of the inner lumen of the first connector and a portion of the inner lumen of the second connector and seal receiving recessed spaces at each end of the central receiving space.

At 204, a portion of the outer lumen of the first connector is inserted into the first recessed space of the airlock.

At 206, the portion of the inner lumen of the first connector is slid through the outer lumen of the first connector to advance the portion of the inner lumen of the first connector into the central receiving space of the airlock.

At 208, a portion of the outer lumen of the second connector is inserted into the second recessed space of the airlock.

At 210, the portion of an inner lumen of the second connector is slid through the outer lumen of the second connector to advance the portion of the inner lumen of the second connector into the central receiving space of the airlock.

Upon the advancement of the inner lumen of the first connector and second connector, the first actuatable seal and the second actuatable seal move from the closed position to the open position and are received by the seal receiving recessed spaces of the airlock such that an outer surface of each actuatable seal is placed into contact with an inner surface of the seal receiving recessed space.

In one or more embodiments, the airlock may further comprise opposing mechanical seals spanning each recessed space in the body to enclose the central receiving space, the mechanical seals being moveable upon application of external force thereupon in order to form an opening to allow the inner lumen of the first connector and the inner lumen of the second connector to enter the central receiving space and be placed in fluid communication.

In one or more embodiments, each mechanical seal may comprise a first and second leaflet that are biased in a closed position to prevent fluid flow within the central receiving space.

In one or more embodiments, each mechanical seal may comprise a destroyable membrane.

In one or more embodiments, each actuatable seal may be biased with a spring such that operation of the spring moves the actuatable seal between the closed position and the open position.

In one or more embodiments, each actuatable seal may comprise a first leaflet and a second leaflet, wherein the first and second leaflets are movable between the closed position and the open position.

In one or more embodiments, when in the open position each actuatable seal may extend outward from the distal end of the outer lumen of the connector.

In one or more embodiments, each actuatable seal may be moveable from the closed position to the open position when an external force is applied to an internal surface of the actuatable seal.

In one or more embodiments, the proximal end of the first connector and the second connector may be adapted to receive tubing.

In one or more embodiments, the central receiving space of the airlock may be sterile.

In one or more embodiments, the central receiving space may include a gasket configured to receive the inner lumen of the first connector and the inner lumen of the second connector.

In one or more embodiments, the gasket may seal a distal end of the inner lumen of the first connector to a distal end of the inner lumen of the second connector.

In one or more embodiments, when the outer surface of each actuatable seal is placed into contact with the inner surface of the seal receiving recessed space aseptic fluid connection is provided.

The present disclosure has described one or more preferred embodiments, and it should be appreciated that many equivalents, alternatives, variations, and modifications, aside from those expressly stated, are possible and within the scope of the invention.

The invention claimed is:

1. A connector system, comprising:
   a first connector extending between a distal end and a proximal end, the first connector comprising:
   an outer lumen,
   an inner lumen that is slidable within the outer lumen of the first connector,
   a first actuatable seal coupled to the distal end of the first connector that is moveable between a closed position that blocks a fluid path of the inner lumen and an open position that allows fluid to flow through the inner lumen of the first connector;
   a second connector extending between a distal end and a proximal end, the second connector comprising:
   an outer lumen,
   an inner lumen that is slidable within the outer lumen of the second connector,
   a second actuatable seal coupled to the distal end of the second connector that is moveable between a closed position that blocks a fluid path of the inner lumen and an open position that allows fluid to flow through the inner lumen of the second connector;
   an airlock comprising a body, the body comprising:
   opposing first and second recessed spaces, wherein the first recessed space is sized to slidably receive a portion of the outer lumen of the first connector and the second recessed space is sized to slidably receive the outer lumen of the second connector;
   a central receiving space that extends between the opposing first and second recessed spaces, the central receiving space having an inner surface sized to receive a portion of the inner lumen of the first connector and a portion of the inner lumen of the second connector and seal receiving recessed spaces at each end of the central receiving space, the seal receiving recessed spaces being sized to receive the first and second actuatable seals,
   wherein the inner lumen of the first connector and the inner lumen of the second connector are slidable to advance into the central receiving space of the airlock, and
   wherein, upon advancement of the inner lumen of the first connector and second connector, the first actuatable seal and the second actuatable seal move from the closed position to the open position and are received by the seal receiving recessed spaces of the airlock such that an outer surface of each actuatable seal is placed into contact with an inner surface of the seal receiving recessed space.

2. The connector system of claim 1, wherein the airlock further comprises opposing mechanical seals spanning each recessed space in the body to enclose the central receiving space, the mechanical seals being moveable upon application of external force thereupon in order to form an opening to allow the inner lumen of the first connector and the inner lumen of the second connector to enter the central receiving space and be placed in fluid communication.

3. The connector system of claim 2, wherein each mechanical seal comprises first and second leaflets that are biased in a closed position to prevent fluid flow within the central receiving space.

4. The connector system of claim 3, wherein each mechanical seal comprises a destroyable membrane.

5. The connector system of claim 4, wherein each actuatable seal is biased with a spring such that operation of the spring moves the actuatable seal between the closed position and the open position.

6. The connector system of claim 5, wherein each actuatable seal comprises a first leaflet and a second leaflet, wherein the first and second leaflets are movable between the closed position and the open position.

7. The connector system of claim 6, wherein when in the open position each actuatable seal extends outward from the distal end of the outer lumen of the connector.

8. The connector system of claim 7, wherein each actuatable seal is moveable from the closed position to the open position when an external force is applied to an internal surface of the actuatable seal.

9. The connector system of claim 8, wherein the proximal end of the first connector and the proximal end of the second connector are adapted to receive tubing.

10. The connector system of claim 9, wherein the central receiving space of the airlock is sterile.

11. The connector system of claim 10, wherein the central receiving space includes a gasket configured to receive the inner lumen of the first connector and the inner lumen of the second connector; and
   wherein the gasket seals a distal end of the inner lumen of the first connector to a distal end of the inner lumen of the second connector.

12. The connector system of claim 11, wherein when the outer surface of each actuatable seal is placed into contact with the inner surface of the seal receiving recessed space, aseptic fluid connection is provided.

13. A method for using a connector system, comprising: providing:
   a first connector comprising an outer lumen, an inner lumen, and a first actuatable seal coupled to a distal end of the first connector that is moveable between a closed position that blocks a fluid path of the inner lumen and an open position that allows fluid to flow through the inner lumen of the first connector, a second connector comprising an outer lumen, an inner lumen, and a second actuatable seal coupled to a distal end of the second connector that is moveable between a closed position that blocks a fluid path of the inner lumen and an open position that allows fluid to flow through the inner lumen of the second connector, and an airlock comprising opposing first and second recessed spaces, and a central receiving space that extends between the opposing first and second recessed spaces, the central receiving space having an inner surface sized to receive a portion of the inner lumen of the first connector and a portion of the inner lumen of the second connector and seal receiving recessed spaces at each end of the central receiving space; inserting a portion of the outer lumen of the first connector into the first recessed space of the airlock; sliding the portion of the inner lumen of the first connector through the outer lumen of the first connector to advance the portion of the inner lumen of the first connector into the central receiving space of the airlock; inserting a portion of the outer lumen of the second connector into the second recessed space of the airlock; sliding the portion of an inner lumen of the second connector through the outer lumen of the second connector to advance the portion of the inner lumen of the second connector into the central receiving space of the airlock; and wherein, upon the advancement of the inner lumen of the first connector and second connector, the first actuatable seal and the second actuatable seal move from the closed position to the open position and are received by the seal receiving recessed spaces of the airlock such that an outer surface of each actuatable seal is placed into contact with an inner surface of the seal receiving recessed space.

*  *  *  *  *